(12) United States Patent
Hähnle et al.

(10) Patent No.: US 6,174,929 B1
(45) Date of Patent: Jan. 16, 2001

(54) WATER-ABSORBENT CROSS-LINKED POLYMERS IN FOAM FORM

(75) Inventors: Hans-Joachim Hähnle, Neustadt; Manfred Walter, Speyer; Jürgen Tropsch, Römerberg; Jens Kremeskötter, Ludwigshafen; Gunnar Schornick, Neuleiningen; Thomas Anstock, Weisenheim, all of (DE)

(73) Assignee: BASF Aktiengesellschaft, Ludwigshaften (DE)

( * ) Notice: Under 35 U.S.C. 154(b), the term of this patent shall be extended for 0 days.

(21) Appl. No.: 09/117,294

(22) PCT Filed: Feb. 27, 1997

(86) PCT No.: PCT/EP97/00962

§ 371 Date: Aug. 26, 1998

§ 102(e) Date: Aug. 26, 1998

(87) PCT Pub. No.: WO97/31971

PCT Pub. Date: Sep. 4, 1997

(30) Foreign Application Priority Data

Feb. 28, 1996 (DE) .............................. 196 07 551

(51) Int. Cl.$^7$ ....................................... C08J 9/28
(52) U.S. Cl. ................... 521/64; 521/149; 522/86
(58) Field of Search ........................ 521/64, 149; 522/86

(56) References Cited

U.S. PATENT DOCUMENTS 5,118,719 * 6/1992 Lind ....................................... 521/64
5,506,035 * 4/1996 Phan ...................................... 521/64

* cited by examiner

*Primary Examiner*—Morton Foelak
(74) *Attorney, Agent, or Firm*—Oblon, Spivak, McClelland, Maier & Neustadt, P.C.

(57) ABSTRACT

Water-absorbing foamlike crosslinked polymers which are obtainable by (I) foaming a polymerizable aqueous mixture which consists of
  (a) monoethylenically unsaturated monomers containing acid groups, which are at least 50 mol % neutralized,
  (b) with or without other monoethylenically unsaturated monomers,
  (c) crosslinker,
  (d) initiators,
  (e) from 0.1 to 20% by weight of at least one surfactant,
  (f) with or without one or more solubilizers and
  (g) with or without thickeners, foam stabilizers, polymerization regulators, fillers and/or cell nucleating agents, the foaming being performed by dispersing fine bubbles of a gas inert to free radicals, and (II) polymerizing the foamed mixture with formation of a foamed hydrogel, with or without adjusting the water content of the foamed polymer to from 1 to 60% by weight, processes for their preparation and their use in sanitary articles which are used for absorbing body fluids and in dressing materials for covering wounds are described.

14 Claims, No Drawings

WATER-ABSORBENT CROSS-LINKED POLYMERS IN FOAM FORM

The invention relates to water-absorbent foamed crosslinked polymers, processes for their preparation and their use in sanitary articles which are used for absorbing body fluids and in dressing materials for covering wounds.

Water-absorbent crosslinked polymers are termed superabsorbent polymers or superabsorbents, because they are able to absorb many times their own weight of aqueous liquids, forming hydrogels. Superabsorbents are used in practice in diapers, for example, for absorbing urine. The superabsorbents have the property of retaining the absorbed liquid even under mechanical loading.

For variation in the performance properties of superabsorbents, two different types of foams are known: (1) mixtures which contain superabsorbents in a foamed matrix, and (2) foams which consist of a superabsorbent material.

A category (1) foam is prepared, for example, from a mixture consisting on the one hand of components for forming a polyurethane foam and on the other hand of polymerizable monomers, a crosslinker and a polymerization initiator for preparing a superabsorbent. From a mixture of this type, in a polycondensation reaction from the polyurethane components, the foam is formed which contains the superabsorbent, resulting from polymerization of the monomers, in the form of an interpenetrating network, cf. U.S. Pat. No. 4,725,628, U.S. Pat. No. 4,725,629 and U.S. Pat. No. 4,731,391.

U.S. Pat. No. 4,985,467 discloses a polyurethane foam which contains a chemically bound superabsorbent. Furthermore, combinations of latex foams are known into which superabsorbent finely particulate materials are incorporated after the foaming process, cf. EP-A-427 219 and U.S. Pat. No. 4,990,541.

Category (2) foams include, for example, products which are obtained by mixing a previously prepared superabsorbent with a polyhydroxy compound and a blowing agent in an extruder at elevated temperature. The foam forms as the mixture is forced out of the extruder. Processes of this type are described, for example, in U.S. Pat. No. 4,394,930, U.S. Pat. No. 4,415,388 and GB-A-2 136 813.

U.S. Pat. No. 4,529,739 and U.S. Pat. No. 4,649,154 disclose processes for preparing foams, in which a water-swellable, carboxyl-bearing material is foamed with a blowing agent which releases the blowing gas in a reaction neutralizing the polymer carboxyls.

According to the information in WO-A-94/22502, superabsorbent foams based on crosslinked partially neutralized polycazboxylates are prepared by foaming a monomer mixture with a water-insoluble blowing agent which has a boiling point below 50° C., and polymerizing the foam to completion virtually simultaneously with foaming.

EP-A-04 21 264 discloses the preparation of foamlike superabsorbents, in which an aqueous monomer mixture containing an emulsified oil phase is polymerized, with the oil occupying the space of the later foam pores and being removed by evaporation, after polymerization is completed, when the foamed material is dried.

WO-A-88/09801 discloses that hydrophilic polymers, eg. poly(sodium acrylate), in the presence of crosslinkers such as polyepoxides and blowing agents, can be processed by heating to give a foamlike superabsorbent.

A procedure for preparing foamlike superabsorbents is also known in which carbonates, hydrogencarbonates or carbon dioxide are added as blowing agent to a mixture of carboxyl-bearing monomers, crosslinking agent and polymerization initiator, polymerization of the monomers being initiated at the same time as the blowing agent is added or shortly thereafter. The superabsorbent is given a foam structure by the carbon dioxide formed in the neutralization reaction, cf. EP-A-2 954 438 and U.S. Pat. No. 4,808,637. According to the process disclosed by WO-A-95/02002, a foamed superabsorbent, following its preparation, is admixed with one or more compounds capable of reacting to form subsequent surface crosslinking and heated to from 100 to 300° C.

In the above-described processes for preparing superabsorbent foams, foam formation and polymerization proceed either synchronously or at insignificantly staggered times. The as yet incompletely polymerized foams have only a short life, generally only a few minutes. A disadvantage of the above-specified processes is, for example, the use of relatively large amounts of blowing agent, in particular the use of CFCs in the case of WO-A-94/22502.

It is an object of the present invention to provide foamed superabsorbents. It is a further object of the present invention to indicate an improved process for preparing foamed superabsorbents.

We have found that these objects are achieved according to the invention with water-absorbing foamlike crosslinked polymers which are obtainable by (I) foaming a polymerizable aqueous mixture which comprises
  (a) monoethylenically unsaturated monomers containing acid groups, which are at least 50 mol % neutralized,
  (b) with or without other monoethylenically unsaturated monomers,
  (c) crosslinkers,
  (d) initiators,
  (e) from 0.1 to 20% by weight of at least one surfactant,
  (f) with or without one or more solubilizers and
  (g) with or without thickeners, foam stabilizers, polymerization regulators, fillers and/or cell nucleating agents,
the foaming being performed by dispersing fine bubbles of a gas inert to free radicals, and
  (II) polymerizing the foamed mixture with formation of a foamed hydrogel, with or without adjustment of the water content of the polymer to from 1 to 60% by weight.

The invention also relates to a process for preparing water-absorbing foamlike crosslinked polymers, which comprises foaming a polymerizable aqueous mixture of
  (a) monoethylenically unsaturated monomers containing acid groups, which are at least 50 mol % neutralized,
  (b) with or without other monoethylenically unsaturated monomers,
  (c) crosslinkers,
  (d) initiators,
  (e) from 0.1 to 20% by weight of at least one surfactant,
  (f) with or without one or more solubilizers and
  (g) with or without thickeners, foam stabilizers, polymerization regulators, fillers and/or cell nucleating agents
in a first process stage by dispersing fine bubbles of a gas inert to free radicals and polymerizing the resulting foam in a second process stage with formation of a foamlike hydrogel, with or without adjustment of the water content of the foamlike hydrogel to from 1 to 60% by weight.

According to the invention, a polymerizable aqueous mixture is processed to form a foam which is stable to processing and can be shaped as desired. The polymerizable aqueous mixture includes as component (a) monoethylenically unsaturated monomers which contain acid groups, which are at least 50 mol % neutralized. Examples of such monomers are monoethylenically unsaturated $C_3$–$C_{25}$-carboxylic acids or anhydrides, for example acrylic, methacrylic, ethacrylic, α-chloroacrylic, crotonic and maleic acids, maleic anhydride, itaconic, citraconic, mesaconic, glutaconic, aconitic and fumaric acids.

In addition, monoethylenically unsaturated sulfonic acids can be used as monomers of the group (a), for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, vinylphosphoric acid, allylphosphonic acid and 2-acrylamido-2-methylpropanesulfonic acid. The monomers can be used alone or in a mixture with each other in the preparation of the superabsorbent foams. Preferred monomers of the group (a) used are acrylic, methacrylic, vinylsulfonic and acrylamidopropanesulfonic acids or mixtures of these, eg. mixtures of acrylic and methacrylic acids, mixtures of acrylic and acrylamidopropanesulfonic acids or mixtures of acrylic and vinylsulfonic acids.

The monomers are at least 50 mol % neutralized with, for example, alkali metal bases or ammonia or amines. Preferably, sodium hydroxide solution or potassium hydroxide solution is used for neutralization. However, the neutralization can also be carried out using sodium carbonate, sodium hydrogencarbonate, potassium carbonate or potassium hydrogencarbonate or other carbonates or hydrogencarbonates or ammonia. The acid groups of the monomers are preferably at least 65 mol % neutralized.

The polymerizable aqueous mixture may contain monomers of the group (b). For the purposes of the invention these are taken to mean other monoethylenically unsaturated monomers which can be copolymerized with the monomers (a) and (c). These include, for example, the amides and nitriles of monoethylenically unsaturated carboxylic acids, eg. acrylamide, methacrylamide and N-vinylformamide, acrylonitrile and methacrylonitrile, dialkyldiallylammonium halides, such as dimethyldiallylammonium chloride, diethyldiallylammonium chloride, allylpiperidinium bromide, N-vinylimidazoles, such as N-vinylimidazole, 1-vinyl-2-methylimidazole, and N-vinylimidazolines, such as N-vinylimidazoline, 1-vinyl-2-methylimidazoline, 1-vinyl-2-ethylimidazoline or 1-vinyl-2-propylimidazoline, which can be used in the polymerization in the form of the free bases, in quaternized form or as salt. Other compounds which are suitable are dialkylaminoalkyl acrylates and dialkylaminoalkyl methacrylates, dimethylaminoethyl acrylate, dimethylaminoethyl methacrylate, diethylaminoethyl acrylate and diethylaminoethyl methacrylate. The basic esters are preferably used in quaternized form or as salt. Further suitable compounds of the group (b) are, for example, vinyl esters of saturated $C_1$–$C_4$-carboxylic acids, such as vinyl formate, vinyl acetate or vinyl propionate, alkyl vinyl ethers having at least 2 carbon atoms in the alkyl group, such as ethyl vinyl ether or butyl vinyl ether, esters of monoethylenically unsaturated $C_3$–$C_6$-carboxylic acids, eg. esters of monohydric $C_1$–$C_{18}$-alcohols and acrylic acid, methacrylic acid or maleic acid, half-esters of maleic acid, eg. monomethyl maleate, and hydroxyalkyl esters of said monoethylenically unsaturated carboxylic acids, eg. 2-hydroxyethyl acrylate, hydroxypropyl acrylate, hydroxybutyl acrylate, hydroxyethyl methacrylate, hydroxypropyl methacrylate and hydroxybutyl methacrylate, N-vinyllactams, such as N-vinylpyrrolidone or N-vinylcaprolactam, acrylic and methacrylic esters of alkoxylated monohydric saturated alcohols, eg. of alcohols having from 10 to 25 carbons which have been reacted with from 2 to 200 mol of ethylene oxide and/or propylene oxide per mole of alcohol, and monoacrylic esters and monomethacrylic esters of poly(ethylene glycol) or poly(propylene glycol), where the molar masses ($M_N$) of the poly(alkylene glycols) can be up to 2000, for example. Other monomers of the group (b) which are suitable are alkyl-substituted styrenes, such as ethylstyrene or tert-butylstyrene. The monomers of the group (b) can also be used in a mixture in the copolymerization with the other monomers, eg. mixtures of vinyl acetate and 2-hydroxyethyl acrylate in any ratio.

The monomers of the group (c) have at least 2 ethylenically unsaturated double bonds. Examples of monomers of this type, which are conventionally used as crosslinkers in polymerization reactions, are N,N'-methylenebisacrylamide, poly(ethylene glycol) diacrylates and poly(ethylene glycol) dimethacrylates, which are each derived from poly(ethylene glycols) of a molecular weight of from 106 to 8500, preferably from 400 to 2000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, diesterified or triesterified with acrylic or methacrylic acid, polyhydric alcohols, such as glycerol or pentaerythritol, triallylamine, tetraallylethylenediamine, divinylbenzene, diallyl phthalate, poly(ethylene glycol)divinyl ethers of poly(ethylene glycols) of a molecular weight of from 126 to 4000, trimethylolpropane diallyl ether, butanediol divinyl ether, pentaerythritol triallyl ether and/or divinylethyleneurea. Preferably, water-soluble crosslinkers are used, eg. N,N'-methylenebisacrylamide, poly(ethylene glycol) diacrylates and poly(ethylene glycol)dimethacrylates, which are derived from addition products of from 2 to 400 mol of ethylene oxide to 1 mol of a diol or polyol, vinyl ethers of addition products of from 2 to 400 mol of ethylene oxide to 1 mol of a diol or polyol, ethylene glycol diacrylate, ethylene glycol dimethacrylate or triacrylates and trimethacrylates of addition products of from 6 to 20 mol of ethylene oxide to one mole of glycerol, pentaerythritol triallyl ether and/or divinylurea.

In addition, compounds can be used as crosslinkers which contain at least one polymerizable ethylenically unsaturated group and at least one further functional group. The functional group of these crosslinkers must be able to react with the functional groups, essentially the carboxyl groups or sulfonic acid groups, of the monomers (a). Examples of suitable functional groups are hydroxyl, amino, epoxy and aziridino groups.

In addition, compounds can be used as crosslinkers which bear at least two functional groups which can react with the carboxyl and sulfonic acid groups of the group (a) monomers used. The suitable functional groups have already been mentioned above, ie. hydroxyl, amino, epoxy, isocyanate, ester, amide and aziridino groups. Examples of crosslinkers of this type are ethylene glycol, diethylene glycol, triethylene glycol, tetraethylene glycol, polyethylene glycol, glycerol, polyglycerol, propylene glycol, diethanolamine, triethanolamine, poly(propylene glycol), block copolymers of ethylene oxide and propylene oxide, sorbitan fatty esters, ethoxylated sorbitan fatty esters, trimethylolpropane, pentaerythritol, poly(vinyl alcohol), sorbitol, poly(glycidyl ethers), such as ethylene glycol diglycidyl ether, poly (ethylene glycol)diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and poly(propylene glycol)diglycidyl ether, polyaziridine compounds, such as 2,2-bishydroxymethylbutanol tris[3-(1-aziridinyl)propionate], 1,6-hexamethylenediethyleneurea, diphenylmethane-bis-4, 4'-N,N'-diethyleneurea, haloepoxy compounds, such as epichlorohydrin and α-methylfluorohydrin, polyisocyanates, such as 2,4-tolylene diisocyanate and hexamethylene diisocyanate, alkylene carbonates, such as 1,3-dioxolan-2-one and 4-methyl-1,3-dioxolan-2-one, polyquaternary amines, such as condensation products of dimethylamine with epichlorohydrin, homo- and copolymers of diallyldimethylammonium chloride and homo- and copolymers of dimethylaminoethyl (meth)acrylate, which may be quaternized with methyl chloride, for example.

Other suitable crosslinkers are polyvalent metal ions which are able to form ionic crosslinks. Examples of crosslinkers of this type are magnesium, calcium, barium and aluminum ions. These crosslinkers are added to the aqueous polymerizable solution as hydroxides, carbonates or hydrogencarbonates, for example.

Other suitable crosslinkers are multifunctional bases which are likewise able to form ionic crosslinks, for example polyamines or their quaternary salts. Examples of polyamines are ethylenediamine, diethylenetriamine, triethylenetetramine, tetraethylenepentamine, pentaethylenehexamine and polyethyleneimines and poly(vinylamines) having molar masses in each case of up to 4,000,000.

In a preferred embodiment of the invention, two different crosslinkers are used, of which one is water-soluble and the other water-insoluble. The hydrophilic crosslinker, which is soluble in the aqueous phase of the reaction mixture, causes in a conventional manner a relatively uniform crosslinking of the resulting polymer, as is customary in the preparation of a superabsorbent. The hydrophobic crosslinker, which is insoluble, or only sparingly soluble, in the polymerizable aqueous mixture, accumulates in the surfactant interface between the gas phase and the polymerizable aqueous phase. As a result, in the subsequent polymerization, the surface of the foam is more extensively crosslinked that the inner part of the superabsorbent hydrogel. A core-shell foam structure is thus obtained directly in the preparation of the superabsorbent foam. An extensive surface crosslinking of this type in a superabsorbent foam is only possible in the known prior art preparation processes by subsequent crosslinking on the surface of a previously formed foamed superabsorbent. For this post-crosslinking, in the conventional procedure, a separate process step is necessary, which can be omitted in the process of the present invention.

Products according to the invention having a core-shell structure exhibit markedly improved properties in comparison with homogeneously crosslinked samples with respect to absorption rate, dispersing action and gel stability. With the exception of polyvalent metal ions, all of the above-described water-insoluble crosslinkers which can be assigned to the different groups are suitable for preparing foams having a core-shell structure, ie. foams in which the entire surface is more extensively crosslinked than the underlying layer, which has been termed the core layer above. Particularly preferred hydrophobic crosslinkers are diacrylates or dimethacrylates or divinyl ethers or alkanediols having from 2 to 25 carbons (branched, linear, with any arrangement of the OH groups), such as 1,3-propanediol, 1,4-butanediol, 1,6-hexanediol, neopentyl glycol, 1,9-nonanediol or 1,2-dodecanediol, di- or tripropylene glycol diacrylates or dimethacrylates, poly(propylene glycol)diacrylates or dimethacrylates, allyl acrylate, allyl methacrylate, divinylbenzene, glycidyl acrylate or glycidyl methacrylate, allyl glycidyl ethers and bisglycidyl ethers of the above-listed alkanediols.

Suitable hydrophilic crosslinkers are, for example, N,N'-methylenebisacrylamide, poly(ethylene glycol)diacrylates or dimethacrylates having a molecular weight $M_N$ of from 200 to 4000, divinylurea, triallylamine, diacrylates or dimethacrylates of addition products of from 2 to 400 mol of ethylene oxide to 1 mol of a diol or polyol or the triacrylate of an addition product of 20 mol of ethylene oxide to 1 mol of glycerol, and vinyl ethers of addition products of from 2 to 400 mol of ethylene oxide to 1 mol of a diol or polyol.

The monomers of the group (a) are present in the polymerizable aqueous mixture, for example, in amounts of from 10 to 80, and preferably from 20 to 60, % by weight. The monomers of the group (b) are only used if appropriate for modifying the superabsorbent foams and can be present in the polymerizable aqueous mixture in amounts of up to 50, preferably in amounts of up to 20, % by weight. The crosslinkers (c) are present in the reaction mixture, for example, at from 0.001 to 5, and preferably from 0.01 to 2, % by weight.

Polymerization initiators which can be used are all initiators forming free radicals under the polymerization conditions which are customarily used in the preparation of superabsorbents. Initiation of polymerization by the action of electron beams on the polymerizable aqueous mixture is also possible. However, the polymerization can also be initiated in the absence of initiators of the abovementioned type by the action of high-energy radiation in the presence of photoinitiators.

Polymerization initiators which can be used are all compounds decomposing into free radicals under the polymerization conditions, eg. peroxides, hydroperoxides, hydrogen peroxide, persulfates, azo compounds and redox catalysts. Preference is given to the use of water-soluble initiators. In some cases it is advantageous to use mixtures of different polymerization initiators, eg. mixtures of hydrogen peroxide and sodium peroxodisulfate or potassium peroxodisulfate. Mixtures of hydrogen peroxide and sodium peroxodisulfate can be used in any ratio. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butylpermaleate, tert-butyl perbenzoate, di(2-ethylhexyl) peroxodicarbonate, dicyclohexyl peroxodicarbonate, di(4-tert-butylcyclohexyl)peroxodicarbonate, dimyristyl peroxodicarbonate, diacetyl peroxodicarbonate, allyl peresters, cumyl peroxyneodecanoate, tert-butyl per-3,5,5-trimethylhexanoate, acetyl cyclohexylsulfonyl peroxide, dilauryl peroxide, dibenzoyl peroxide and tert-amyl perneodecanoate. Particularly suitable polymerization initiators are water-soluble azo starters, eg. 2,2'-azobis(2-amidinopropane)dihydrochloride, 2,2'-azobis(N,N'-dimethylene)isobutyramidine dihydrochloride, 2-(carbamoylazo)isobutyronitrile, 2,2'-azobis[2-(2'-imidazolin-2-yl)propane]dihydrochloride and 4,4'-azobis(4-cyanovaleric acid). Said polymerization initiators are used in customary amounts, eg. in amounts of from 0.01 to 5, preferably from 0.1 to 2.0, % by weight, based on the monomers to be polymerized.

Suitable initiators are, in addition, redox catalysts. The redox catalysts include as oxidizing component at least one of the abovementioned per compounds and, as reducing component, for example, ascorbic acid, glucose, sorbose, ammonium or alkali metal hydrogen sulfite, ammonium or alkali metal sulfite, ammonium or alkali metal thiosulfate, ammonium or alkali metal hyposulfite, ammonium or alkali metal pyrosulfite or ammonium or alkali metal sulfide, metal salts, such as iron(II) ions or silver ions or sodium hydroxymethylsulfoxylate. Preferably, ascorbic acid or sodium sulfite is used as the reducing component of the redox catalyst. Based on the amount of monomer used in the polymerization, for example, from $3 \cdot 10^{-6}$ to 1 mol % of the reducing component of the redox catalyst system is used, and from 0.001 to 5.0 mol % of the oxidizing component of the redox catalyst.

If the polymerization is triggered by the action of high-energy radiation, as initiator use is customarily made of photoinitiators. These can be, for example, α-cleavage compounds, H-abstracting systems or else azides. Examples of such initiators are benzophenone derivatives, such as Michler's ketone, phenanthrene derivatives, fluorene derivatives, anthraquinone derivatives, thioxanthone derivatives, coumarin derivatives, benzoin ethers and their derivatives, azo compounds such as the free-radical formers mentioned above, substituted hexaarylbisimidazoles or acylphosphine oxides. Examples of azides are: 2-(N,N-dimethylamino)-ethyl 4-azidocinnamate, 2-(N,N-dimethylamino)-ethyl 4-azidonaphthyl ketone, 2-(N,N-dimethylamino)-ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone. The photoinitiators, if used, are customarily employed in amounts of from 0.01 to 5% by weight, based on the monomers to be polymerized.

The polymerizable aqueous mixtures contain as component (e) from 0.1 to 20% by weight of at least one surfactant. The surfactants are of critical importance for the preparation and stabilization of the foam. Anionic, cationic or nonionic surfactants or surfactant mixtures which are compatible with one another may be used. Low-molecular-weight or polymeric surfactants may be used, combinations of different types or of the same types of surfactants having been proved to be advantageous. Nonionic surfactants are, for example, addition products of alkylene oxides, in particular ethylene oxide, propylene oxide and/or butylene oxide, to alcohols, amines, phenols, naphthols or carboxylic acids. Advantageously, surfactants used are addition products of ethylene oxide and/or propylene oxide to alcohols containing at least 10 carbons, the addition products containing from 3 to 200 mol of added ethylene oxide and/or propylene oxide per mole of alcohol. The addition products contain the alkylene oxide units in the form of blocks or in random distribution. Examples of nonionic surfactants are the addition products of 7 mol of ethylene oxide to 1 mol of tallow fatty alcohol, reaction products of 9 mol of ethylene oxide with 1 mol of tallow fatty alcohol and addition products of 80 mol of ethylene oxide to 1 mol of tallow fatty alcohol. Other commercial nonionic surfactants comprise reaction products of oxo alcohols or Ziegler alcohols having 5 to 12 mol of ethylene oxide per mole of alcohol, in particular having 7 mol of ethylene oxide. Other commercial nonionic surfactants are obtained by ethoxylation of castor oil. 12 to 80 mol, for example, of ethylene oxide are attached per mole of castor oil. Other commercial products are, for example, the reaction products of 18 mol of ethylene oxide with 1 mol of tallow fatty alcohol, the addition products of 10 mol of ethylene oxide to 1 mol of a $C_{13}/C_{15}$-oxoalcohol, or the reaction products of 7 to 8 mol of ethylene oxide to 1 mol of a $C_{13}/C_{15}$-oxoalcohol. Other suitable nonionic surfactants are phenolalkoxylates, such as p-tert-butylphenol, which is reacted with 9 mol of ethylene oxide, or methyl ethers of reaction products of 1 mol of a $C_{12}$–$C_{18}$ alcohol and 7.5 mol of ethylene oxide.

The above-described nonionic surfactants can be converted, for example by esterification with sulfuric acid, into the corresponding half-esters of sulfuric acid. The half-esters of sulfuric acid are used as anionic surfactants in the form of the alkali metal salts or ammonium salts. Examples of anionic surfactants which are suitable are alkali metal or ammonium salts of half-esters of sulfuric acid of addition products of ethylene oxide and/or propylene oxide to fatty alcohols, alkali metal or ammonium salts of alkylbenzenesulfonic acid or of alkylphenol ether sulfates. Products of said type are commercially available. For example, the sodium salt of a sulfuric acid half-ester of a $C_{13}/C_{15}$-oxoalcohol reacted with 106 mol of ethylene oxide, the triethanolamine salt of dodecylbenzenesulfonic acid, the sodium salt of alkylphenol ether sulfates and the sodium salt of the sulfuric acid half-ester of a reaction product of 106 mol of ethylene oxide with 1 mol of tallow fatty alcohol are commercial anionic surfactants. Other suitable anionic surfactants are sulfuric acid half-esters of $C_{13}/C_{15}$ oxo alcohols, paraffinsulfonic acids such as $C_{15}$-alkylsulfonate, alkyl-substituted benzenesulfonic acids and alkyl-substituted naphthalenesulfonic acids such as dodecylbenzenesulfonic acid and di-n-butylnaphthalenesulfonic acid, and fatty alcohol phosphates such as $C_{15}/C_{18}$ fatty alcohol phosphate. The polymerizable aqueous mixture can comprise combinations of a nonionic surfactant and an anionic surfactant or combinations of nonionic surfactants or combinations of anionic surfactants. Cationic surfactants are also suitable. Examples of these are the dimethyl sulfate-quaternized reaction products of 6.5 mol of ethylene oxide with 1 mol of oleylamine, distearyldimethylammonium chloride, lauryltrimethylammonium chloride, cetylpyridinium bromide and dimethyl sulfate-quaternized stearic ester of triethanolamine, which is preferably used as cationic surfactant.

The surfactant content of the polymerizable aqueous mixture is from 0.1 to 20, preferably from 0.5 to 10% by weight. In most cases, the polymerizable aqueous mixtures have a surfactant content of from 1.5 to 6% by weight.

The polymerizable aqueous mixtures may include as component (f) at least one solubilizer. For the purposes of the invention these are water-miscible organic solvents, eg. alcohols, glycols, poly(ethylene glycols) and monoethers derived therefrom, in which case the monoether molecules do not contain double bonds. Suitable ethers are methyl glycol, butyl glycol, butyl diglycol, methyl diglycol, butyl triglycol, 3-ethoxy-1-propanol and glycerol monomethyl ether.

The polymerizable aqueous mixtures comprise from 0 to 50% by weight of one or more solubilizers. If solubilizers are used, their content in the polymerizable aqueous mixture is preferably up to 25% by weight.

The polymerizable aqueous mixture may contain thickeners, foam stabilizers, polymerization regulators, fillers and cell nucleating agents. Thickeners are used, for example, for optimizing the foam structure and for improving the foam stability, so that the foam shrinks only slightly during the polymerization. Suitable thickeners are all natural and synthetic polymers known for this purpose which greatly increase the viscosity of an aqueous system. These can be water-swellable or water-soluble synthetic and natural polymers. Suitable thickeners are also pulverulent superabsorbents. An extensive overview of thickeners is found, for example, in the publications by R. Y. Lochhead and W. R. Fron, Cosmetics & Toiletries, 108, 95–135 (May 1993) and M. T. Clarke, "Rheological Additives" in D. Laba (ed.) "Rheological Properties of Cosmetics and Toiletries", Cosmetic Science and Technology Series, Vol. 13, Marcel Dekker Inc., New York 1993.

Suitable water-swellable or water-soluble synthetic polymers suitable as thickeners are, for example, high-molecular-weight polymers of the monoethylenically unsaturated monomers containing acid groups as described under (a), for example homopolymers of acrylic acid and/or methacrylic acid or slightly crosslinked copolymers of acrylic acid and/or methacrylic acid and a compound which contains at least two ethylenically unsaturated double bonds, eg. butanediol diacrylate. Compounds which are also suitable are high-molecular weight polymers of acrylamide and methacrylamide or copolymers of acrylic acid and acrylamide having molar masses of more than one million. Copolymers of this type are known as thickeners. Known thickeners are also high-molecular-weight poly(ethylene glycols) or copolymers of ethylene glycol and propylene glycol and high-molecular-weight polysaccharides such as starch, guar seed meal, carob bean meal or derivatives of natural substances such as carboxymethylcellulose, hydroxyethylcellulose, hydroxymethylcellulose, hydroxypropylcellulose and cellulose mixed ethers. A further group of thickeners are water-insoluble products, such as finely divided silicon dioxide, pyrogenic silicic acids, precipitated silicic acids in hydrophilic or hydrophobic forms, zeolites, titanium dioxide, cellulose powders or other finely divided powders of crosslinked polymers different from superabsorbers. Polymerizable aqueous mixtures can comprise the thickeners in amounts of up to 30% by weight. When thickeners of this type are used, they are present in an amount of from 0.1, preferably from 0.5 to 20, % by weight in the polymerizable aqueous mixture.

To optimize the foam structure, hydrocarbons having at least 5 carbons in the molecule may be added to the aqueous reaction mixture. Examples of suitable hydrocarbons are pentane, hexane, cyclohexane, heptane, octane, isooctane, decane and dodecane. Suitable aliphatic hydrocarbons can be straight-chain, branched or cyclic and have a boiling point above the temperature of the aqueous mixture during foaming. The aliphatic hydrocarbons prolong the life of the as yet unpolymerized foamed aqueous reaction mixture. This facilitates the handling of the unpolymerized foams and enhances the process reliability. The hydrocarbons are used in amounts of from 0 to 10% by weight, based on the polymerizable aqueous mixture. When used, the amounts present in the aqueous mixture are preferably from 0.1 to 5% by weight.

To vary properties of the superabsorbents, for example the absorption rate and the absorption capacity for water, it can be advantageous to add a polymerization regulator or a mixture of a plurality of polymerization regulators to the aqueous reaction mixture. Examples of suitable regulators are formic acid, thio compounds such as 2-mercaptoethanol, mercaptopropanol, mercaptobutanol, dodecylmercaptan, thioglycolic acid or amines such as ethanolamine, diethanolamine, triethanolamine, triethylamine, morpholine or piperidine. The amounts of polymerization regulators can be up to 10% by weight, based on the monomers used. If polymerization regulators are used, they are preferably employed at from 0.1 to 5% by weight, based on the monomers.

The constituents specified under (g), which may be present or absent, if employed can be used individually or in a mixture in the preparation of the polymers according to the invention. However, the procedure can be carried out in the absence of thickeners, foam stabilizers, fillers, cell nucleating agents and polymerization regulators.

In the preparation according to the invention of water-absorbent foamed crosslinked polymers, the above-described polymerizable aqueous mixture is foamed in a first process step. For this purpose, a gas which is inert to free radicals is dispersed in the aqueous monomer phase in the form of fine bubbles so that a foam forms. The gas bubbles are introduced using, for example, beating, shaking, stirring or whipping apparatus. In addition, it is possible to produce foams of this type by gases exiting from a liquid-covered orifice or by exploiting turbulence phenomena in flows. Finally, formation of lamellae on wires or screens can be utilized for this purpose. These diverse methods may if appropriate be combined with one another. Examples of suitable gases inert to free radicals are nitrogen, carbon dioxide, helium, neon and argon. Preferably, nitrogen is used.

Foaming and polymerization are preferably performed separately. The polymerizable aqueous mixture can be foamed, for example, in industrial equipment which is known for producing urea/formaldehyde foams, cf. Frisch and Saunders, Polymeric Foams Part II, pp. 679 ff. (1973). In the laboratory, the polymerizable aqueous mixture can be foamed most simply with a conventional kitchen appliance which is fitted with egg whisks. The whipped foam is preferably produced in an inert gas atmosphere. Examples of inert gases which can be used are nitrogen, noble gases or carbon dioxide. To produce the foam, all components of the reaction mixture are combined. Expediently, all water-soluble components are first dissolved in water and only then are the water-insoluble substances added. Depending on which whipped foam production process is used and on the initiator present in the polymerizable aqueous mixture, it can also be advantageous not to add the initiator to the mixture until the end of the whipping process. The consistency of the whipped foams can be varied within a broad range. It is thus possible to produce light flowing whipped foams or else stiff sliceable foams. The mean size of the gas bubbles, their size distribution and their arrangement in the liquid matrix can likewise be varied in a broad range by the choice of surfactants, the solubilizers, thickeners and foam stabilizers, cell nucleating agents, temperature and whipping technique, so that the density, open-cell character or wall thickness of the matrix material can be set in a simple manner. The temperatures of the polymerizable aqueous mixture during the foaming operation are in the range from –10 to 100, preferably from 0 to +50° C. Foam production temperatures are always employed which are below the boiling point of constituents of the polymerizable aqueous mixture. The foam can also be produced under elevated pressure, eg. at from 1.5 to 25 bar. However, atmospheric pressure is preferably employed.

In comparison with the processes known hitherto for producing foamed superabsorbents, a critical advantage of the preparation of such foams according to the invention is that in the first process stage of the process according to the invention, foamed, polymerizable aqueous mixtures are obtained which are stable over a relatively long period, eg.

up to 6 hours, so that, for example, they may be handled without problem. The as yet unpolymerized foamed mixtures can, for example, be brought into a suitable shape for the subsequent polymerization, in order to produce the shaped bodies desired for a particular application. The waste foam possibly arising in the shaping of the foamed polymerizable aqueous mixture can be readily recycled to the process. The foamed polymerizable material, for example, can be applied in the desired thickness to a temporary support material which is advantageously furnished with a nonstick coating. The foam can, for example, be knife-coated onto a base. Another possibility is to charge the polymerizable foamed aqueous mixture into molds which likewise have a nonstick coating and to polymerize the foam to completion therein.

Since the foamed polymerizable aqueous mixture has a long life, this mixture is also suitable for producing composite materials. Thus, for example, the polymerizable foam, after the whipping process, can be applied to a permanent support material, eg. polymer films (eg. films made of polyethylene, polypropylene or polyamide) or metal foils, webs, fluff, tissues, fabrics, natural or synthetic fibers, or to other foams. In the production of composite materials, under some circumstances it can also be advantageous to apply the polymerizable foam in the form of defined structures or in different layer thicknesses to a support material. However, it is also possible to apply the polymerizable foam to fluff layers and to impregnate them so that, after the polymerization, the fluff is an integral constituent of the foam. The foamed polymerizable aqueous mixture obtainable in the first process stage can also be shaped to form large blocks and polymerized. The blocks, after the polymerization, can be cut or sawn to form smaller shaped bodies. Sandwich-type structures can also be produced by applying a foamed polymerizable aqueous mixture to a base, covering the foamed layer with a film, webs, tissues, fabrics, fibers or other foams which may consist of a different material from the base first used and again applying foam, with or without a further covering of film, webs, tissues, fabrics, fibers or other foams. The composite is then subjected to polymerization in the second process stage. However, sandwich-type structures having further foam layers can also be produced.

In the second stage of the process for preparing the superabsorbent foams according to the invention, the foamed polymerizable aqueous mixture is polymerized. Depending on the initiator used, the polymerization can be carried out by temperature elevation, by the action of light, by irradiation with electron beams or else by temperature elevation and the action of light. The temperature of the foamed polymerizable aqueous mixture can be increased by all processes customary in industry, for example bringing the foam into contact with heatable plates, the action of infrared radiation on the polymerizable foam, or microwave heating. Foam layers of the invention having a layer thickness of up to about 1 millimeter are produced, for example, by heating from one side or, in particular, by irradiation from one side. If thicker foam layers are to be produced, eg. foams several centimeters thick, microwave heating of the polymerizable foamed material is particularly advantageous, because relatively uniform heating can be achieved in this manner. Polymerization is carried out in this case, for example, at from 20 to 180° C., preferably from 20 to 100° C.

Foam layers of moderate thicknesses, that is having a thickness from about 1 millimeter to about 2 centimeters, for example from about 2 millimeters to about 1 centimeter, are preferably produced in the following manner: instead of initiating the polymerization on one surface only, it is initiated on two surfaces by subjecting a layer of the foamed mass according to the invention to heat treatment and/or light irradiation on both surfaces. The two surfaces of the foamed layer can, according to the invention, be treated synchronously or asynchronously or staggered in time in any desired time sequence. For example, both part-surfaces of a foam layer can be heat-treated simultaneously or staggered in time once or repeatedly per part-surfaces. The same procedure can be used with light irradiation. However, there is also the possibility of treating each part-surface not only with heat but also with light, heat and light being able to act simultaneously or in any desired sequence, once or repeatedly on the same part-surface of the foam layer. However, it is usually most expedient to apply heat and/or light once per part-surface of the foam layer.

Since the heat treatment is expediently performed by contact heating and the support material used for this is usually opaque, two-sided initiation of polymerization is most expediently performed by contact heating one part-surface and, for example, simultaneous irradiation of the opposite part-surface. This process variant and two-sided contact heating are suitable, in particular, for producing composite materials.

In the case of two-sided initiation of polymerization, the heat treatment is usually carried out in a range from about 50 to about 200° C., preferably at from about 80 to about 160° C., with typical contact times of from about 0.5 to about 25 minutes per part-surface of the foam layer, preferably at from about 2 to about 15 minutes. Light from the UV/visible region is preferably used for the irradiation, for example light having a wavelength of from greater than about 200 nm to about 750 nm, for example from about 250 nm to about 700 nm, for instance UV-A radiation of wavelength from 315 to 400 nm. The duration of irradiation can likewise be in the range of from about 0.5 to about 25 minutes, preferably from about 1 to 10 minutes, per part-surface of the foam layer.

In the case of combined heat treatment and irradiation of the same or opposite part-surfaces of the foam layer, the respective duration of heat treatment and irradiation can be identical or different. Depending on composition and thickness of the foam layer, the type and amount of polymerization initiators used, intensity and wavelength of the light and temperature of the contact heating apparatus and other criteria, it can, however, be advantageous, to carry out heat treatment and irradiation over time periods of different lengths. The time periods chosen can, for example, follow sequentially in time. For example, a 3-minute heating of the first part-surface can be followed by, for example, a 2-minute irradiation of the opposite second part-surface. This may be followed, for example, by a 2-minute heat treatment of the first and/or the second part-surface. This treatment rhythm may be repeated, if appropriate, once or repeatedly, retaining or changing the selected time periods. However, the time periods selected can also overlap. For example, the irradiation can be maintained for only part of the heat-treatment period. Thus, for example, the first part-surface of the foam layer can be heated, for example for 2 minutes, and then heated, eg., for a further 4 minutes and, in synchrony therewith, the opposite surface can be irradiated for 4 minutes. It is likewise conceivable to heat or irradiate the two part-surfaces at first, eg. for 3 minutes, in synchrony and then to continue the heat treatment of the one part-surface, eg. for 2 minutes, after the irradiation of the other part-surface has ended. This treatment cycle can also, if appropriate, be repeated once or repeatedly, retaining or changing the selected time intervals.

When polymerization is initiated by the action of light on the foamed polymerizable material, all conventional sources of illumination can be employed, if their emission spectrum is adapted to the photoinitiator used. When the polymerization is initiated by illumination, a combination of a photoinitiator with a thermal initiator is advantageously used, or else a photoinitiator is advantageously used which can also act as a thermal initiator, eg. azo initiators. Since the foam heats greatly during the polymerization owing to the high heat of polymerization, this thus achieves a particularly fast and effective course of the polymerization reaction. When polymerization is initiated by the action of light, the polymerization temperature is in the range from 0 to 150, preferably from 10 to 100° C.

An essential advantage of the process of the invention is that the polymerization proceeds with substantial retention of the structure of the foamed polymerizable aqueous mixture, ie. the polymerizable foam changes only insignificantly in volume during the polymerization. The polymerization reaction is influenced by the starting temperature, the initiation method or the heat removal. The polymerization temperature is preferably controlled to prevent boiling of the polymerizable aqueous mixture. As polymerization proceeds, solidification of the foam occurs owing to increasing gel formation. After polymerization is complete, a foamed hydrogel is present which contains from 30 to 80% by weight of water. The foam, at least in part, has an open-cell structure. For the use of the foam as a superabsorbent, a residual moisture of from 1 to 60, preferably from 15 to 35, % by weight is desirable. The foamed hydrogel produced in the polymerization is therefore usually dried. To obtain a flexible foam, it must have a certain residual moisture content. The water content is highly dependent on the density of the foam produced. The higher the density, the greater the residual moisture which must be set. Therefore, an upper limit of from 35 to 60% by weight of water can be highly expedient. If a batch having a very high solids content is polymerized giving a foam having a very high density, it may even be necessary to further moisten the foam after the polymerization in order to obtain the necessary flexibility.

The foam can be dried using conventional methods, for example by heating with a hot gas stream, by applying vacuum, by infrared irradiation, or by microwave heating, which last again proves advantageous here in the drying of large-volume shaped bodies.

By means of the process of the invention, a predominantly or at least partially open-cell superabsorbent foam is obtained which is relatively hard and brittle in the completely dried state. However, for many applications flexible foams are demanded, but the relatively hard and brittle foam initially obtained can be made flexible. This can be achieved using external plasticizers or by internal flexibilization.

External plasticizers are components which, in addition to the gel-forming components, are either added to the reaction mixture prior to foaming, or are applied to the foam afterwards. Examples of plasticizers which are used are hydrophilic and hygroscopic substances. External flexibilization is primarily achieved by the specific setting of a defined residual water content. In addition, the flexibilization can be improved by the use of, for example, polyols such as glycerol, poly(alkylene glycols) such as poly(ethylene glycols) or poly(propylene glycols), or cationic surfactants. Examples of suitable cationic surfactants are dimethylsulfate-quaternized reaction products of 1 mol of oleylamine with 5 to 10 mol of ethylene oxide, distearyldimethylammonium chloride, lauryltrimethylammonium chloride, cetylpyridinium bromide and ethanolamine esters of long-chain fatty acids such as diethanolamine stearate, ethanolamine stearate and triethanolamine stearate, which is preferably used as external plasticizer.

Internal flexibilization of the foam is the use of plasticizing components which are incorporated into the gel structure. These components may be substances which themselves bear unsaturated groups and are present in the polymerizable aqueous mixture as monomer (b) in the polymerization and are conjointly incorporated into the gel structure, or they react with the gel-forming material. The internal plasticizer is intended to decrease the glass temperature of the polymer comprising the superabsorbent. Examples of internal plasticizers are olefins, esters of ethylenically unsaturated $C_3$–$C_5$-carboxylic acids and monohydric $C_2$–$C_{30}$ alcohols or poly(ethylene glycol)monoesters or poly(propylene glycol)monoesters of monoethylenically unsaturated $C_3$–$C_5$-carboxylic acids. For internal flexibilization, monomers (b) are suitable which decrease the glass temperature of the copolymers formed with the monomers (a), eg. vinyl esters of saturated carboxylic acids containing at least 4 carbons, alkyl vinyl ethers having at least 2 carbons in the alkyl, vinyllactams and alkyl-substituted styrenes such as ethylstyrene.

As has already been disclosed above, an inhomogeneous density of crosslinking can be produced in the novel superabsorbent foams even during their production. This is particularly advantageous if use is made as monomers of the above described components (a) acrylic acid, methacrylic acid, vinylsulfonic acid, acrylamidopropanesulfonic acid or their mixtures and (c) a mixture of at least one water-soluble and at least one water-insoluble crosslinker.

Nevertheless, it can be desirable to modify the degree of crosslinking of the foam later. In order to achieve this aim, for example, latent crosslinking sites can be incorporated into the gel during polymerization by adding suitable monomers which do not lead to crosslinking reactions under the conditions of foam production, but, under specific conditions which can be employed later, eg. as a result of greatly elevated temperature, are able to form further crosslinking points in the gel structure. An example of the use of monomers of this type is the incorporation of hydroxyl-containing compounds which, at elevated temperature, ie. above 150° C., are able to react with the carboxyls in the foam structure. Examples of suitable compounds which have latent crosslinking sites are hydroxyethyl acrylate, hydroxypropyl acrylate, hydroxybutyl acrylate, monoacrylic esters of glycerol, monoacrylates or monomethacrylates of poly(ethylene glycols) containing at least 2 ethylene glycol units, monoacrylates or monomethacrylates of poly (propylene glycols) containing at least 2 propylene glycol units and monomethacrylates of polyhydric alcohols, eg. hydroxybutyl methacrylate, hydroxypropyl methacrylate, hydroxyethyl methacrylate or glycerol monomethacrylate.

A further potential method for homogeneous post-crosslinking is the subsequent addition of crosslinking reagents, ie. compounds having at least two reactive groups which, under suitable conditions, eg. on heating to above 70° C., are able to react with the acid groups of the foamed hydrogel. In this case it is also possible to modify the inhomogeneous density of crosslinking, under the control of the depth penetration of the crosslinker. Suitable crosslinkers form covalent or ionic bonds with the polymer matrix carboxyls; they are compounds which have at least two functional groups of identical or different types, eg. hydroxyl, amino, quaternary ammonium, isocyanato, epoxy, aziridino, ester or amide. Preferred crosslinkers are polyhydric alcohols such as glycerol or bisepoxides. The crosslinkers may be applied to the foamed material by spraying, dipping or gas-phase precipitation, for example.

The novel superabsorbent foams have, for example, a density of from $10^{-3}$ to 0.9, preferably from 0.05 to 0.7, g/cm$^3$. The foam density is determined gravimetrically by cutting squares having sides of length 5 cm, for example, with a sharp knife from a uniform foam layer having a defined thickness between 3 and 5 mm. The samples are weighed and the weight obtained is divided by the volume calculated from the dimensions.

To determine the contents extractable from the foamed superabsorbent, a dried and ground foam sample is dispersed in a 0.9% strength by weight sodium chloride solution and the dispersion is stirred for 1 hour. The foamed material is then filtered off and the amount of extractable content in the filtrate determined by titrimetry.

The water absorption capacity per gram of foamed superabsorbent is determined on foam pieces having a thickness of 3 mm, each weighing 1 g. Retention is studied in this case by the teabag test. The liquid used in the test is a 0.9% strength sodium chloride solution. 1 g of the foamed material is then placed in a teabag which is then sealed, care being taken to ensure that the teabag leaves sufficient space for complete swelling. The teabag is then immersed in the liquid for a defined time and after draining for 10 minutes is reweighed. For calculation of the absorption capacity, a blank test must be carried out in which a teabag not containing the foamed superabsorbent is immersed in the solution and the weight of the teabag is determined after the above specified draining time of 10 minutes. The absorption capacity is then given by the following equation (1):

$$\text{Absorption capacity} = \frac{\text{Weight of teabag containing superabsorbent foam} - \text{weight of teabag in blank test}}{\text{Initial weight of superabsorbent foam}} \quad (1)$$

The retention is determined as follows:

The same procedure is followed as above, but instead of draining, the teabag is centrifuged for 3 min at an acceleration of 250 g. Retention is calculated using the following equation (2):

$$\text{Retention} = \frac{\text{Weight of teabag after centrifuging} - \text{Weight of teabag in blank test}}{\text{Initial weight of superabsorbent foam}} \quad (2)$$

The absorption speed (AS below) was determined by cutting 1 g rectangular samples from foam layers having a uniform thickness of 3 mm using a sharp knife, pouring 20 g of synthetic urine over the samples in a Petri dish, and measuring with a stopwatch the time required for the foam to absorb the synthetic urine completely. The absorption speed (AS) in g/g.sec is calculated from the following equation (3):

$$AS = 20 \text{ g}/[1 \text{ g} * \text{time measured (in sec)}] \quad (3)$$

In addition, in this test, the uniformity of liquid absorption is assessed according to a 6-point scale. The ratings 1–6 have the following meanings:

1: The foam swells homogeneously from the beginning.
2: The foam swells homogeneously after a few seconds.
3: The foam swells homogeneously after 30 sec.
4: The foam swells inhomogeneously the whole time, but only a small part is affected.
5: The foam swells inhomogeneously the whole time, but a considerable part is affected.
6: The foam swells the whole time at the surface only.

Synthetic Urine Formula

The Following Salts are Dissolved in 1 l of Distilled Water 2.00 g of KCl
2.00 g of $Na_2SO_4$
0.85 of $NH_4H_2PO_4$
0.15 g of $(NH_4)_2HPO_4$
0.19 g of $CaCl_2$
0.23 g of $MgCl_2$ The salts used must be anhydrous.

Foam stability in the swollen state

The stability of the swollen material was assessed using a 4-point scale on the samples obtained in the above test. The ratings 1–4 have the following meanings:

1: The foam can be removed undamaged from the Petri dish and can be bent through 180° without it tearing.
2: The foam can be removed undamaged from the Petri dish.
3: The foam tears on being removed from the Petri dish.
4: The foam disintegrates to form a loose gel heap.

The above described water-absorbent, foamed crosslinked polymers can be employed for all purposes for which the foamed superabsorbents described in the literature are used. They are employed, for example, in sanitary articles which are used for absorbing body fluids and in dressing materials for covering wounds. They are suitable, for example, as a water-absorbent component in diapers, sanitary towels and incontinence articles. They can be used in the form of composite materials. Foamed superabsorbents can, in addition, be used as sealing material, as soil improver, as soil substitute and as packaging material. Special designs of articles which contain foamed superabsorbents are described extensively in WO-A-94/22502, for example. The foamed superabsorbents are, in addition, suitable for dewatering sludges, for thickening waterborne paints, eg. for disposing of residual amounts of unused waterborne paints or dyes, eg. by adding pulverulent foamed superabsorbents to waterborne paint residues until solidification occurs. The foamed, water-absorbent, crosslinked polymers can, in addition, be used for dehydrating water-containing oils. They can be used in the above described applications in the form of a powder, for example, having a mean particle diameter of from 150 $\mu$m to 5 mm.

Owing to their properties, the above described foams can fulfill various functions in hygiene articles in the storage of body fluids:

acquisition
distribution and/or
storage

The storage of body fluids is undertaken completely by the foams, whereas for acquisition and distribution, other constituents such as high loft-nonwovens, polypropylene webs, polyester webs or chemically modified celluloses may, if appropriate, be used for reinforcement as a layer on the foams.

The percentages in the Examples are by weight, unless the context implies otherwise.

EXAMPLES

Example 1

The following components are mixed in a glass beaker using a magnetic stirrer:

224.23 g of a 37.3% strength sodium acrylate solution in water 49.68 g of water 21.36 g of acrylic acid 3.15 g of the product of adding 80 mol of ethylene oxide to 1 mol of tallow fatty alcohol 1.58 g of pentane 1.05 g of the triacrylic ester of glycerol etherified with 20 mol of ethylene oxide 0.53 g of 1,4-butanediol diacrylate The resulting homogeneous mixture is placed in a 2 l flask, into which argon is introduced from the bottom. Two egg whisks, each of which is connected to a type RW 20 DZM Janke & Kunkel stirrer, are inserted into the flask. The argon stream is set so that it bubbles through the reaction mixture at a rate of 80 l/hour. The two stirrers are initially set to a speed of 60 rpm. 45.00 g of finely ground superabsorbent (particle size<100 µm) are added to the reaction mixture and mixed in homogeneously. The free flask opening is virtually completely sealed with parafilm and the stirrer speed is set to 1000 rpm. The mixture is whipped at this speed for 20 min. 5 min before whipping is ended, 11.9 g of a 3% strength aqueous solution of 2,2'-azobis(2-amidinopropane) dihydrochloride are added to the flask. After the whipping period is ended, a fine-cell, readily flowable whipped foam is obtained.

The foam is poured into a teflon-coated aluminum mold (width 10 cm, length 20 cm) having a 3 mm-high rim and polymerized for 6 min on a conventional hotplate (Ceran 500) at 125° C., while it is simultaneously irradiated from the other side with a UV lamp (UV 1000 from Höhnle).

The foam layer obtained is completely dried in a vacuum drying cabinet at 70° C. A portion of the completely dried sample is pulverized for determination of the extractable contents. The remaining portion is adjusted to a water content of 25% with distilled water, the moistened foam being kept overnight in a sealed polyethylene bag for equilibration.

The test results obtained are summarized in Table 1.

Example 2

Example 1 is repeated, except that the foam is this time polymerized to completion for 6 min between two teflon-coated aluminum plates, which are heated to a temperature of 120° C., in a layer thickness of 3 mm.

The test results obtained are summarized in Table 1.

Example 3

Example 1 is repeated except that the foam is this time spread onto a glass plate in a layer thickness of 3 mm. The foam sample is irradiated from both sides synchronously for 4 min with two UV lamps, as used in Example 1.

The test results obtained are summarized in Table 1.

Example 4

Example 1 is repeated, except that the foam is this time applied in a layer thickness of 2 mm.

The test results obtained are summarized in Table 1.

Example 5

Example 1 is repeated, except that the foam is this time applied in a layer thickness of 4 mm.

The test results obtained are summarized in Table 1.

Example 6

Example 1 is repeated, except that the foam is this time applied in a layer thickness of 6 mm.

The test results obtained are summarized in Table 1.

Example 7

The following components are mixed homogeneously overnight in a screw-cap bottle on a roller stand:

224.23 g of a 37.3% strength sodium acrylate solution in water 21.36 g of acrylic acid 1.10 g of trimethylolpropane triacrylate 4.20 g of the sodium salt of a sulfuric acid half-ester of a $C_{13/15}$-oxoalcohol 1.10 g of Natroxol 250 H4 BR (hydroxyethylcellulose from Aqualon GmbH and Co. KG)

100 g of the above mixture are whipped in a Bosch kitchen appliance having two whisks at mixing speed 4 under $CO_2$ to form a foam. 4.00 g of a 3% strength aqueous solution of 2,2'-azobis(2-amidinopropane)dihydrochloride and 5 g of pentane are then added and the mixture is stirred for a further 5 min. A fine-cell, readily flowing whipped foam is obtained.

The further procedure corresponds to that of Example 1.

The test results obtained are summarized in Table 1.

Comparison Example 1

Example 1 is repeated, except that the 3 mm high foam is this time polymerized for 6 min by one-sided heating on a conventional hotplate at 125° C.

The test results obtained are summarized in Table 2.

Comparison Example 2

Example 1 is repeated, except that the foam is this time irradiated with the above described UV lamp for 6 min at a layer thickness of 3 mm.

The test results obtained are summarized in Table 2.

Comparison Example 3

Example 1 is repeated, except that the foam is this time poured into a rectangular polypropylene vessel (width 20 cm, length 20 cm) in a layer thickness of 3 mm and polymerized for 5 min in a microwave oven having a power of 2250 w.

The test results obtained are summarized in Table 2.

Comparison Example 4

Example 1 is repeated, except that the foam is this time irradiated on one side with an infrared lamp of a power of 60 W for 8 min at a layer thickness of 3 mm.

The test results obtained are summarized in Table 2.

Comparison Example 5

Example 1 is repeated, except that the foam is this time heated from one side for 6 min and irradiated from the other side with the infrared lamp of the type above.

The test results obtained are summarized in Table 2.

Comparison Example 6

Example 5 is repeated, except that the foam is irradiated for 6 min through the glass plate with the UV lamp described in Example 1, while it is simultaneously irradiated with the above-described infrared lamp from the free side.

The test results obtained are summarized in Table 2.

TABLE 1

Properties of the foams according to the invention

| Ex. No. | Appearance of the foam layer | Density [g/cm$^3$] | Absorption[a] [g/g] | Retention[b] [g/g] | Extractables [%] | AS[c] [g/g sec] |
|---|---|---|---|---|---|---|
| 1 | Open-cell foam structure, uniform on both sides, no unpolymerized foam residues | 0.52 | 23.5 | 10.1 | 9.0 | 0.91 |
| 2 | Open-cell foam structure, uniform on both sides, no unpolymerized foam residues | 0.48 | 24.1 | 10.3 | 8.0 | 0.80 |
| 3 | Open-cell foam structure, uniform on both sides, no unpolymerized foam residues | 0.53 | 22.8 | 9.8 | 9.3 | 0.95 |
| 4 | Open-cell foam structure, uniform on both sides, no unpolymerized foam residues | 0.46 | 23.3 | 9.7 | 11.1 | 1.24 |
| 5 | Open-cell foam structure, uniform on both sides, no unpolymerized foam residues | 0.49 | 21.8 | 9.5 | 10.4 | 0.89 |
| 6 | Open-cell foam structure, uniform on both sides, no unpolymerized foam residues | 0.51 | 23.6 | 10.2 | 9.2 | 0.77 |
| 7 | Open-cell foam structure, uniform on both sides, no unpolymerized foam residues | 0.49 | 23.4 | 10.5 | 9.2 | 1.35 |

[a]Absorption capacity determined according to equation (1)
[b]Retention determined according to equation (2)
[c]Absorption speed determined according to equation (3)

TABLE 2

Properties of foams not according to the invention

| Ex. No. | Appearance of the foam layer | Density [g/cm$^3$] | Absorption[a] [g/g] | Retention[b] [g/g] | Extractables Anteile [%] | AS[c] [g/g sec] |
|---|---|---|---|---|---|---|
| 1 | Pronounced skin formation on the unheated side, slight skin formation on the heated side | 0.55 | 23.5 | 10.4 | 9.3 | <0.06 |
| 2 | Open-cell foam structure on the irradiated side, unpolymerized residues on the unirradiated side | 0.46 | 21.8 | 9.2 | 15.8 | 1.18 |
| 3 | Several holes of diameter between 1 and 3 cm with unpolymerized foam | 0.49 | 21.6 | 8.9 | 0.49 | — |
| 4 | Highly pronounced skin formation on the infrared irradiated side, small amounts of unpolymerized foam residues on the unirradiated side | 0.53 | 22.8 | 9.0 | 14.3 | 0.14 |
| 5 | Highly pronounced skin formation on the infrared irradiated side, open-cell structure on the contact-heated side | 0.55 | 23.6 | 10.1 | 10.2 | 0.15 |
| 6 | Highly pronounced skin formation on the infrared irradiated side, open-cell structure on the UV-heated side | 0.56 | 22.9 | 9.8 | 9.5 | 0.18 |

[a]Absorption capacity determined according to equation (1)
[b]Retention determined according to equation (2)
[c]Absorption speed determined according to equation (3)

We claim:

1. A process for preparing water-absorbing foamlike crosslinked polymers, which comprises foaming a polymerizable aqueous mixture of (a) monoethylenically unsaturated monomers containing acid groups, which are at least 50 mol % neutralized, (b) with or without other monoethylenically unsaturated monomers, (c) crosslinkers, (d) with or without one or more polymerization initiators, (e) from 0.1 to 20% by weight of at least one surfactant, (f) with or without one or more solubilizers and (g) with or without thickeners, foam stabilizers, polymerization regulators, fillers and/or cell nucleating agents in a first process stage by dispersing fine bubbles of a gas inert to free radicals and polymerizing the resulting foam in a second process stage with formation of a foamed hydrogel, the polymerization being started by contact heating and/or irradiating with light from the UV/visible region a layer of the foamed mixture on both surfaces.

2. A process as claimed in claim 1, wherein a part-surface of the mixture is heated and the opposite part-surface is irradiated with light.

3. A process as claimed in claim 1, wherein the heat treatment is carried out by contact heating at from about 50 to 200° C.

4. A process as claimed in claim 1, wherein a treatment is performed simultaneously or sequentially in any desired time sequence.

5. A process as claimed in claim 1, wherein as monomers use is made of
   (a) acrylic acid, methacrylic acid, vinylsulfonic acid, acrylamidopropanesulfonic acid or their mixtures, and
   (c) a mixture of at least one water-soluble and at least one water-insoluble crosslinker.

6. A process as claimed in claim 1, wherein, as water-soluble crosslinkers (c), use is made of acrylic and methacrylic esters of at least dihydric alcohols, or methylenebisacrylamide.

7. A process as claimed in claim 1, wherein, as surfactants (e), use is made of addition products of ethylene oxide and/or propylene oxide to alcohols containing at least 10 carbons, the addition products containing from 3 to 200 mol of ethylene oxide and/or propylene oxide as adduct per mole of alcohol.

8. A process as claimed in claim 1, wherein, as surfactants (e), use is made of alkali metal salts or ammonium salts of sulfuric acid half-esters of addition products of ethylene oxide and/or propylene oxid to fatty alcohols, alkali metal salts or ammonium salts of alkylbenzenesulfonic acids or of alkylphenol ether sulfates.

9. A process as claimed in claim 1, wherein, as surfactants (e), use is made of quaternization products of tertiary amines or amine esters which contain at least one $C_{10}$–$C_{18}$-alkyl radical.

10. A process as claimed in claim 1, wherein, as thickeners, use is made of water-swellable or water-soluble synthetic or natural polymers.

11. A process as claimed in claim 1, wherein, as thickeners, use is made of pulverulent superabsorbents.

12. A process as claimed in claim 1, wherein, as stabilizers for the foamed aqueous mixtures, use is made of aliphatic hydrocarbons whose boiling point is above the temperature of the aqueous mixture during the foaming.

13. A water-absorbing foamlike crosslinked polymer which is obtainable by a process according to claim 1.

14. The process of claim 1, further comprising setting the water content of said foamed hydrogel to from 1 to 60% by weight.

* * * * *

UNITED STATES PATENT AND TRADEMARK OFFICE
CERTIFICATE OF CORRECTION

PATENT NO. : 6,174,929

DATED : Jan. 16, 2001

INVENTOR(S): Hans-Joachim Hähnle, et al.

It is certified that an error appears in the above-identified patent and that said Letters Patent is hereby corrected as shown below:

On the title page, Item (73), the Assignee's city of residence is incorrect. Item (73) should read as follows:

(73) Assignee: BASF Aktiengesellschaft,
Ludwigshafen (DE)

Signed and Sealed this

Fifteenth Day of May, 2001

Attest:

NICHOLAS P. GODICI

Attesting Officer

Acting Director of the United States Patent and Trademark Office